United States Patent [19]

Hiltebrandt

[11] 4,169,476
[45] Oct. 2, 1979

[54] APPLICATOR FOR SURGICAL CLIP

[75] Inventor: Siegfried Hiltebrandt, Knittlingen, Fed. Rep. of Germany

[73] Assignee: Wolf Medical Instruments Corporation, Rosemont, Ill.

[21] Appl. No.: 824,065

[22] Filed: Aug. 12, 1977

[51] Int. Cl.² .................. A61B 17/10; A61B 17/12
[52] U.S. Cl. .................................. 128/325; 128/346; 72/410; 29/243.56
[58] Field of Search ........... 128/325, 326, 321, 334 R, 128/346, 303 R, 337; 72/410; 29/243.56

[56] References Cited

U.S. PATENT DOCUMENTS

| 3,882,854 | 5/1975 | Hulka et al. ............... 128/321 X |
| 4,064,881 | 12/1977 | Meredith ....................... 128/325 |

Primary Examiner—Henry J. Recla
Attorney, Agent, or Firm—Kinzer, Plyer, Dorn & McEachran

[57] ABSTRACT

An applicator for a spring-biased surgical clip, including a pair of independently moveable push rods of which one is moveable distally against a first spring bias while both are moveable proximally against a second spring bias.

12 Claims, 6 Drawing Figures

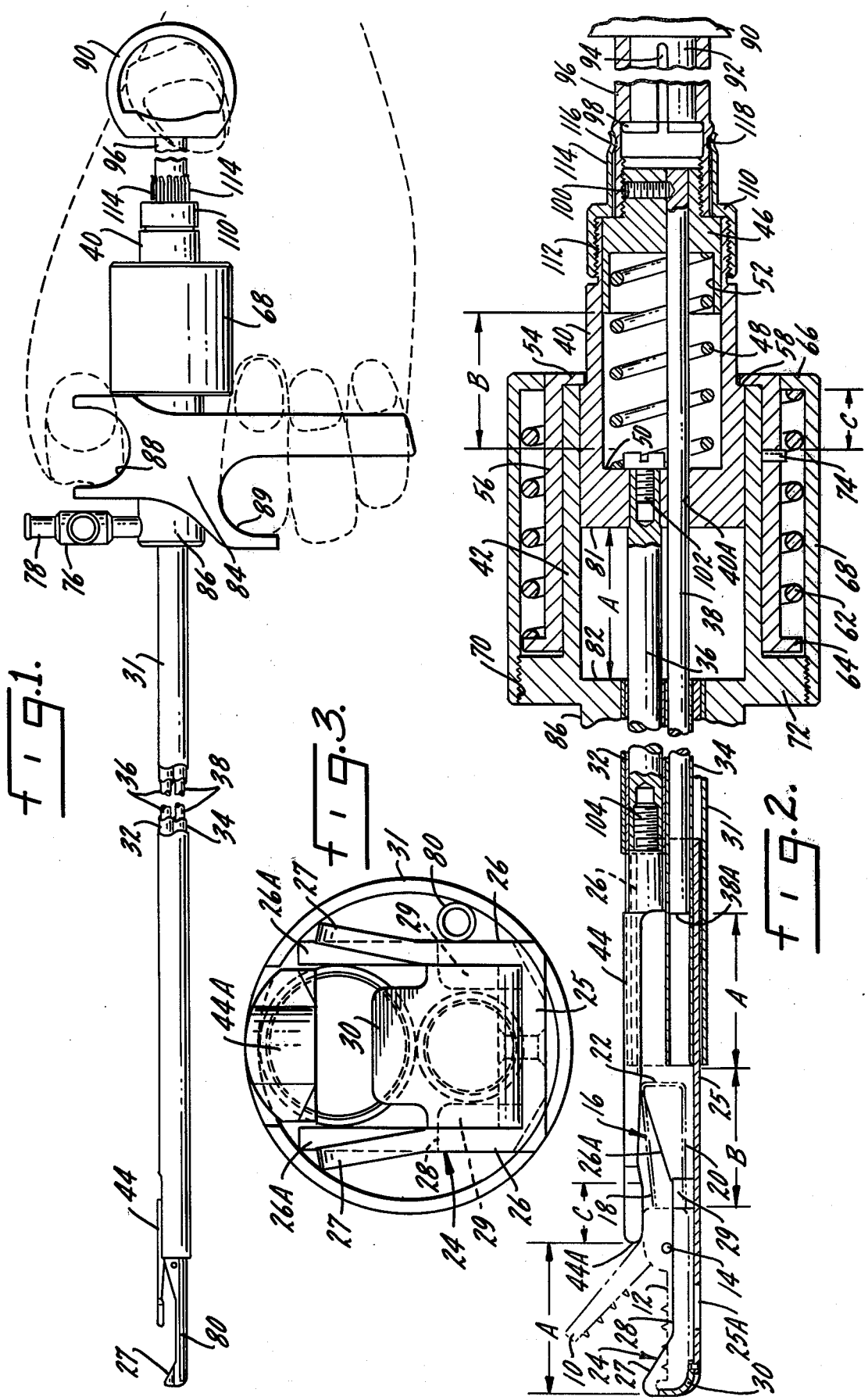

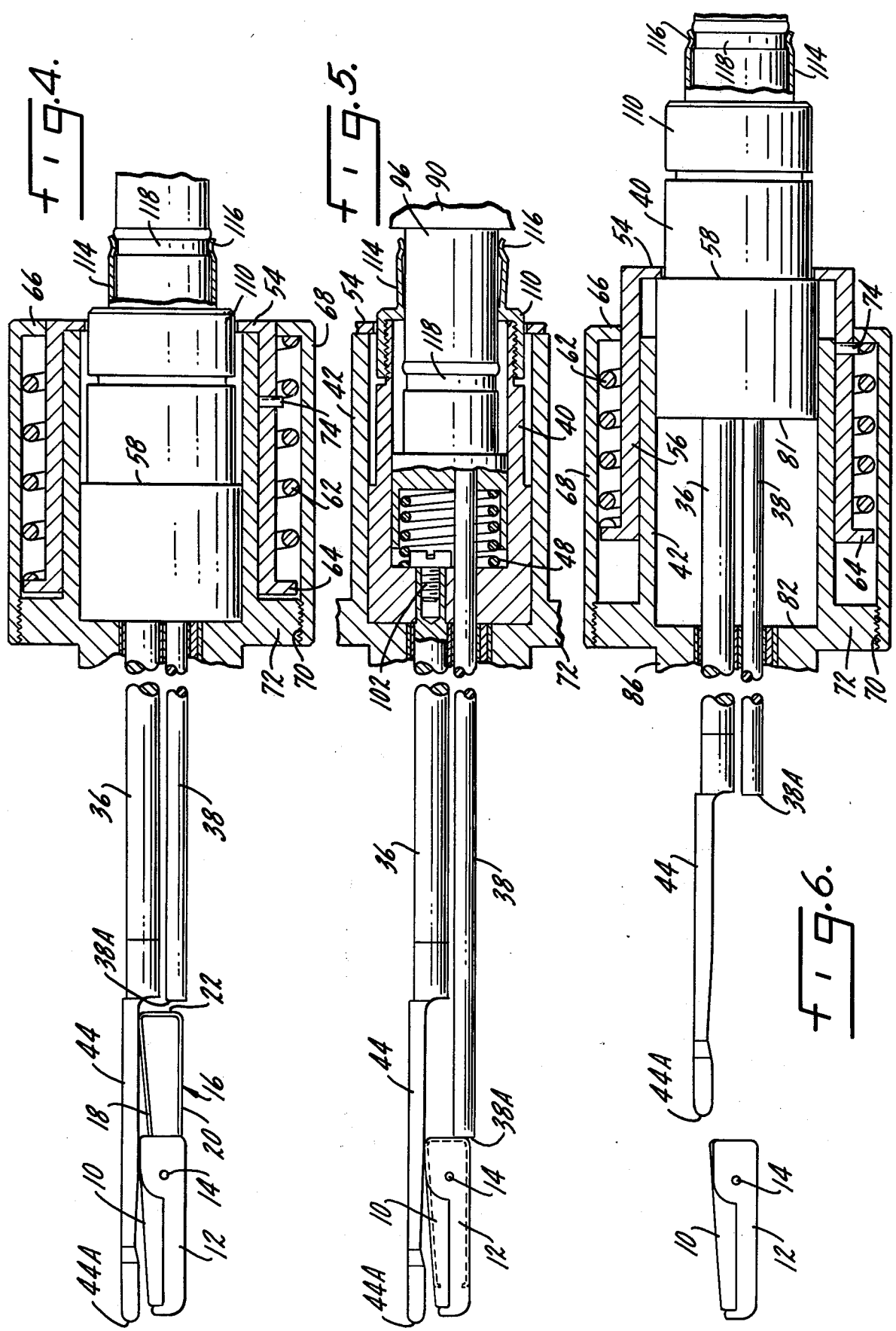

APPLICATOR FOR SURGICAL CLIP

This invention relates to an applicator for applying a surgical clip to produce necrosis in the tissue of a Fallopian tube.

The primary object of the invention is to devise an applicator having bi-directional syringe motions familiar to a surgeon and to enable the surgeon to apply a clip without having necessarily to shift the position of the fingers on the instrument between the time the clip is associated with the applicator and the time the applicator is withdrawn from the woman's body leaving the clip attached to the Fallopian tube.

Another object of the invention is to incorporate in the applicator a spring detent which allows the surgeon to sense (to feel) manually that the instrument and the clip are in coordinated position for the final motion which characterizes completion of the operation except for removal of the instrument from the body of the patient.

Another object of the invention is to employ the same detent as an indicator of the parts of the instrument being in position for reverse thumb thrust.

Specifically it is an object of the present invention, first, to associate two plungers (each supporting a push rod for coordination with the clip) and two springs in such a manner that the surgeon may perform the operation while using both a forward syringe-type motion and a reverse syringe-type motion accomplished entirely by the thumb; and, second, to uniquely combine a spring detent with the foregoing so the surgeon can "feel" certain positions.

IN THE DRAWING:

FIG. 1 is a side elevation of the instrument, partly broken away;

FIG. 2 is a fragmented sectional view of the instrument on a larger scale compared to FIG. 1;

FIG. 3 is an end view of the instrument on a larger scale than FIG. 2, and showing the instrument in the "safe open" position;

FIGS. 4, 5 and 6 are elevational views, similar to FIG. 1 but on the scale of FIG. 2, showing the instrument in three other positions.

The clip is a Hulka-Clemens type having a pair of normally open jaws 10 and 12, hinged at 14, for closure on the fallopian tube. All parts of the clip are biologically inert. The jaws are normally held open by bent-over free ends (not shown) of a thin U-shaped clip spring 16 having two legs 18 and 20 joined by a bight or cross arm 22.

The clip is described with more detail in application Ser. No. 652,616, filed Jan. 26, 1976 now U.S. Pat. No. 4,112,951. By closing the upper jaw 10 in one motion and then sliding the spring 16 forwardly (distally) in a second motion the jaws may be permanently clamped on the fallopian tube initially located between the jaws. Surgeons describe instruments from the standpoint of the part nearest the hand ("proximal") and the part farthest from the hand, "distal"; those terms will be employed herein.

The applicator includes, at the distal end, a cradle 24 adapted to receive the clip. The cradle is a metal stamping, box-like in shape, having a long bottom wall 25 and a pair of long side walls 26 inserted as a unit into the distal end of an outer tube as will be described.

The distal end portions of the side walls of the cradle are sloped downwardly at 27, FIG. 2, and as shown in FIG. 3 these side wall portions are outwardly divergent so the clip may be easily inserted therebetween. The medial portions of the side walls are recessed at 28 so the clip when inserted may be easily seen and preferably the bottom wall has an opening 25A so the surgeon may look for distinctive coloration of the clip in home position. The proximal portions of the side walls then rise gradually at 26A. A pair of stops 29 are secured to the inside surfaces of the side walls, engageable by the rear of the clip when properly inserted. When the clip is properly inserted the spring 16 extends rearwardly.

The cradle is completed by a separate end wall 30 secured to the distal end of the bottom wall 25. The inner surface of the end wall is concave, neatly to engage complementally the distal end of the clip when inserted.

The applicator comprises an outer tube 31 in which are positioned first and second guide sleeves 32 and 34. A first push rod 36 is positioned in the first guide sleeve for longitudinal forward movement therein from the retracted position shown in FIG. 2 and a second push rod 38 is similarly positioned in the second tube. The first rod is used manually to close the upper jaw 10; the second rod is used manually to close the spring 16.

The cradle 24, as noted, is inserted into the distal end of the tube 31 and is fixed therein as by solder.

The first push rod 36 has a proximal end secured, as shown in FIG. 2, to a first hollow plunger 40 reciprocal in a guide cylinder 42. An actuator extension 44, for closing the upper jaw 10, is separably attached to the distal end of the first rod 36. In the normal position of the applicator, when the clip is being inserted in the cradle, the actuator 44 is retracted of course, but in the retracted position the free end 44A thereof applies a slight force to the upper jaw of the clip when the latter is fully inserted (placing spring 16 under slight tension and closing jaw 10 by a very slight amount) thereby securing the clip against accidental displacement. Nonetheless, the clip may be removed manually. The first push rod when fully thrust forward closes the upper jaw 10, but the clip is not necessarily locked closed at this time.

The second push rod 38 is secured to a plunger 46 coaxial with and nested inside plunger 40 so as to be guided thereby, just as cylinder 42 serves as a guide for plunger 40. Rod 38 extends freely through an opening 40A in plunger 40. Plunger 46 is biased rearwardly by a coil spring 48 surrounding rod 38. The coil spring 48 has one end 50 bearing against an internal end wall presented at the forward or distal end of plunger 40 and the opposite end seated in a recess 52 in the end of plunger 40. Spring 48 is a flexible coupling between plungers 40 and 46.

As shown in FIG. 2, rod 38 has a free distal end 38A normally positioned a considerable distance behind the bight or cross leg of clip spring 16. Rod 38 is used to close spring 16 but only after jaw 10 has been previously closed by rod 36.

Displacement of plunger 40 proximally from cylinder 42 is prevented by a radial inwardly directed stop flange 54 at one end of a sleeve or collar 56 which surrounds cylinder 42, flange 54 engaging an annular shoulder 58 formed on the outer surface of plunger 40. This stop is spring biased for reasons to be explained.

Sleeve 56 also serves as a retainer for a second, stronger coil spring 62 which surrounds sleeve 56. Thus, sleeve 56 has a second, distal flange 64, directed radially outward, at the end of sleeve 56 opposite the stop flange 54. One end of spring 62 engages flange 64 and the opposite end of spring 62 engages an inwardly directed flange 66 on an outermost bushing 68 having a threaded end 70 screwed to a nut 72 formed on an enlargement of cylinder 42. Spring 62 is normally under slight compression regulated by turning bushing 68 in one direction or the other.

A stop pin 74, extending radially outward, is secured to sleeve 56 in a position displaced from flange 66 for reasons to be explained.

A fitting 76 may be secured to cylinder 42, having a nipple 78 to which a flexible hose (not shown) may be connected to enable a "local" anesthetic or other fluid to be delivered to the abdomen through a small tube 80 opening at the distal end of the instrument.

Since spring 48 couples the plungers they may be advanced together, over distance A, by a force applied to a proximal end extension of plunger 46 in a manner to be explained. This motion closes the upper jaw of the clip. Forward travel of plunger 40, over distance A, is limited by the forward end 81 thereof engaging the internal end wall 82 of cylinder 42 which constitutes a stop. Thereafter, by a second applied force, plunger 46 may be advanced independently through distance B, compressing coil spring 48 until the distal end of the second push rod has forced the clip spring to home position, locking the clip jaws in fully closed position.

The applicator may be held in the familiar manner of a syringe and the rods moved back and forth by the thumb. To this end, a strut of plastic 84 is press-fitted on the outer surface of a reduced section 86 of cylinder 42, forward of the enlarged nut portion 72. Strut 84 has a small cradle 88 for the index finger and a larger cradle 89 for the other three fingers whereby the applicator may be aimed and held steady by the fingers while the thumb is used to apply a force along the axis of the outer tube 31. To enable the thumb to be used, a thumb ring 90 is formed at one end of a plastic plug 92. Plug 92 is slotted at 94 so it may be contracted and inserted into a sleeve 96 threadedly attached as an extension to the proximal end of plunger 46. The plug 92 has a locking ring 98 thereon adapted to expand into a corresponding groove inside sleeve 96. Both plungers are coaxial with the outer tube 31; consequently the thumb force will be applied along the axis of tube 31.

Rod 38 is secured to plunger 46 by a set screw 100. Rod 36 is secured to plunger 40 by a screw 102 and the actuator 44 is secured to rod 36 by a screw 104.

As noted above, the upper jaw 10 of the clip is forcefully engaged and thereby captured at the free end of the actuator 44, when inserted in the cradle 24; accidental displacement of the clip is thereby prevented as the surgeon prepares for insertion. This (FIG. 2) is termed the "outside safe open" position of the clip. Incidental to insertion of the applicator through an operating trocar sleeve, positioned in an abdominal incision near the navel, the the clip is closed by extending distally the free end of the actuator 44 travelling forwardly (through distance A) over the upper surface of the jaw 10 which gradually closes. The actuator 44 is thus extended by pressing forwardly on ring 90 with the thumb, causing plunger 40 to move forwardly in cylinder 42 until wall 81 engages wall 82. During forward movement of rod 36, rod 38 travels along over the same distance since at this time spring 48 is merely a coupling between the two plungers. Thus, no spring pressure of the applicator is involved at this time, spring 16 of the clip is not actuated, nor has the instrument yet been inserted in the trocar. This is termed the "outside safe closed" position of the clip (FIG. 4) because clip jaw 10 will spring open if a back force is applied by the thumb in ring 90.

Now, with the jaws closed, or even beforehand, the surgeon inspects the fallopian tube either through the optic of a laparoscope, if that route is being used, or through an optic positioned in a second trocar inserted through a second incision near the navel, or by direct incision into the abdomen by laparotomy or minilaparotomy, or by direct incision through the vagina to the abdominal cavity via posterior culpotomy. Assured of a good operating site, the surgeon thereupon operatively inserts the distal end of the present applicator; then, when inside the abdomen, rod 36 is retracted by reverse thumb movement so the clip is in the "inside safe open" position (same as FIG. 2) as the surgeon moves the open clip toward the fallopian tube. Again, actuator 44, though retracted, applies a slight holding force to the rear of the clip.

When the clip jaws have embraced the fallopian tube, rod 36 is again actuated in the forward direction, closing jaws 10 and 12 on the fallopian tube, resulting in the "inside safe closed" position, corresponding to FIG. 4. When jaw 10 is closed, the actuating end 38A of rod 38 is still displaced a few mm. behind clip spring 16 as will be evident from FIG. 4. When the surgeon is satsified the fallopian tube is operatively captured a strong thumb thrust is exerted by means of ring 90 to extend the second rod 38, through distance B, against the return force of spring 48. This thrust moves the free end 38A of the second rod into contact with the adjacent end of spring 16, FIG. 5, so that legs or wings of the clip spring move distally over the outer surfaces of the clip jaws and finally attain the free ends of the clip jaws, permanently locking the two in the "spring closed" position, FIG. 5.

To withdraw the applicator, the thumb force on ring 90 is relaxed, allowing spring 48 to expand, retracting rod 38 by the distance B. Thereafter, a rearward thrust on ring 90 by the thumb retracts both cylinders 46 and 40 simultaneously, retracting over distance A, so that the parts are restored to the position shown in FIG. 2. A third movement is involved, FIG. 6, as will now be described.

It is advantageous for the surgeon to have the assurance of being forewarned that the clip is in the "safe closed" position, FIG. 4, ready for actuation of the spring 16 to lock the jaws in the fully closed position about the fallopian tube. I attain this feature of safety by constructing the applicator so the surgeon can sense, by feel, that the clip is in "ready" position to be locked and to this end a spring detent is employed to offer resistance to the final forward thumb thrust. Thus, as shown in FIG. 2, a bushing 110 is threaded onto a proximal extension 112 of the first plunger. The bushing 110 has a proximal extension of reduced diameter presenting a plurality of spring fingers 114, the free ends of which are bent to afford inwardly convex spring tensioned tips 116 fitting forcefully in an annular groove 118 in the sleeve 96 which receives the thumb plug 92.

The resistance of the spring tips 116 exceeds the thumb force necessary to actuate the plungers over distance A when the two plungers travel together to cause the upper jaw 10 to be closed. That is, the mere, slight force of the thumb necessary to so operate the plungers 46 and 40 in unison is insufficient to disengage the spring tips 116, which offer resistance to independent movement of the second plunger. The surgeon can feel this resistance and can maneuver with the assurance of being able to hold the clip in the "ready" or "safe open" position at the fallopian site before deciding to exert the final thumb thrust overcoming the spring detent 116, especially in the instance of a difficult patient.

It has already been explained the clip in the "safe open" position, FIG. 2, is captured by the distal end 44A of the actuator 44 in its retracted position. Inside the patient, after the jaws are locked closed and the actuator 44 fully retracted through distance A (after first retracting over distance B) incidental to withdrawing the instrument back through the operating trocar, the distal end of the actuator reposes on the hinged end of the locked clip and must be further retracted to release the clip from the cradle 24, which is the "full open" position shown in FIG. 6. Thus, the upper rod is pulled rearwardly from the position shown in FIG. 2 to the position shown in FIG. 6. Such further retraction is permitted by spring 62, overcome by a strong return thrust by the thumb, sufficient to overcome spring detent 116, whereby plunger 40 is retracted by a slight distance (C) enough to displace the actuator end 44A entirely from the clip, (to the "full open" position) allowing the cradle 24 to be sliped off the clip in the proximal direction and separated from the clip which is now fastened on the body tissue. The limit of retraction over distance C is defined by pin 74 engaging flange 66 as a stop. When the clip is thus released to complete the operation, the thumb force may be either relaxed or maintained as the instrument is removed from the abdomen.

The friction fit of plunger 40 inside cylinder 42 simulates the familiar feel of a syringe in both directions of movement and this is also true of the resistance offered by spring 48 during compression, and by spring 62 when it is compressed to release the clip inside the body of the patient.

Cradle 88 for the index finger enables the thumb force easily to be applied. Cradle 88 may be ring-shaped if desired and a second ring, accomodating only the middle finger, may be used in place of cradle 89. Thus, the strut 84 may be replaced by two finger rings or any other attachment allowing at least two fingers to oppose the thumb.

We claim:

1. An applicator for applying a hinged clip to a fallopian tube, in which the clip has a pair of normally open jaws, one to be closed on the other and then the two locked by a clasp spring slidably supported on the jaws for movement to an actuated jaw locking position, said applicator comprising an outer tube containing both an axially moveable first push rod having a free end including means for closing the one jaw and a second axially moveable push rod having a free end including means for actuating the spring, a cradle supported at the forward distal end of the outer tube to support the clip with the open jaw adjacent the free end of the first push rod, a guiding cylinder attached to said outer tube, a first plunger slidably disposed within said guiding cylinder and having said first rod attached thereto, a second plunger slidably mounted in the first plunger and having the second push rod attached thereto, first spring means tending to bias the second plunger to a retracted position inside the first plunger and flexibly coupling the second plunger to the first whereby a forward thrust exerted by the thumb on the second plunger causes both plungers and both rods to move forwardly in unison from a retracted position within said guiding cylinder, a first stop on said cylinder for limiting forward movement of the first plunger and first rod to a position where said one jaw has been closed while the second rod remains displaced from the clip spring, whereafter a further thrust by the thumb compresses said first spring allowing the second rod to move forwardly to actuate the clip spring, and a rearward extension on the second plunger enabling thumb pressure to be exerted.

2. An applicator according to claim 1 having an attachment dependent from and supported by the guiding cylinder enabling at least two fingers to oppose thumb thrust.

3. An applicator according to claim 1 wherein the first push rod in its retracted position engages the open jaw of the clip in the cradle, thereby to capture and retain the clip in the cradle said applicator comprising a second moveable stop engaging the first plunger in its retracted position, said applicator including second spring means applying a forward force to the second stop for limiting the first plunger in its retracted position, whereby the captured clip may be released by a reverse thrust applied to the first plunger in excess of the force applied by said second spring means.

4. An applicator according to claim 3 including spring detent means and wherein the second plunger is r restrained against forward movement by said spring detent means which detent means releases in a fashion sensed by the surgeon as an incident to thrusting the second plunger forwardly with sufficient force to overcome the spring detent means and to actuate the clip spring.

5. An applicator according to claim 4 in which the first stop is presented by an end wall of the cylinder in which the first plunger is disposed, in which the first spring is concentric within both plungers, and in which the second stop is presented by a sleeve slidably mounted on said cylinder.

6. An applicator according to claim 1 including a duct extending from the distal end of the clip cradle toward the proximal end of the applicator and communicating with a nipple on the applicator allowing a fluid to be introduced thereby into the abdomen.

7. An applicator for applying a hinged clip to a fallopian tube, in which the clip has a pair or normally open jaws, one to be closed on the other and then the two locked by a clasp spring slidably supported on the jaws for movement to an actuated jaw locking position, said applicator comprising an axially moveable first push rod having a free end including means for closing the one jaw and a second axially moveable push rod having a free end including means for actuating the spring, a guide surrounding said push rods, a cradle supported at the distal end of the applicator to support the clip having the open jaw adjacent the free end of the first push rod, a first plunger attached to said first rod and being slidably disposed in said guide, a second plunger attached to said second push rod and being slidably supported within the first plunger, first spring means tending to bias the second plunger to a retracted position inside said first plunger and flexibly coupling the second plunger to the first plunger whereby a forward thrust exerted by the thumb on the second plunger causes both plungers and both rods to move toward the cradle forwardly in unison from a retracted position, first stop means on the applicator for limiting forward movement of the first plunger and rod to a position where said one jaw has been closed while the first spring means holds the second rod displaced from the clip spring, whereafter a further thrust by the thumb compresses said first spring means allowing the second plunger and rod to move forwardly to actuate the clip spring, and an extension on the second plunger enabling thumb pressure to be exerted on the first and second plunger.

8. An applicator according to claim 1 having an attachment dependent from and supported by said guide enabling the thumb thrust to be opposed by at least two fingers.

9. An applicator according to claim 7 wherein the first push rod in its retracted position engages the open jaw of the clip in the cradle, thereby to capture and retain the clip in the cradle, said applicator comprising a second moveable stop engaging the first plunger in its retracted position and second spring means applying a forward force to said moveable stop for limiting the first plunger in its retracted position, whereby the captured clip may be released by a reverse thrust applied to the first plunger in excess of the force applied by said second spring means.

10. An applicator according to claim 7 including spring detent means which offers resistance to advancing the second plunger to actuate the clip spring.

11. In a surgical clip applicator having a reciprocal extendable and retractable actuator means for applying, on forward extendable motion, a hinged clip to a fallopian tube, in which the clip has a pair of normally open jaws, one to be closed on the other and then the two locked in closed position by a clasp spring slidably supported on the jaws for movement to an actuated jaw locking position, the applicator including an elongated housing surrounding the actuator means and having at its distal end a cradle to support the clip with the open jaw aligned with the actuator means, the improvement comprising:

said actuator means having an axially extended portion outside the housing at the proximal end of the housing and so configured as to enable thumb force to be applied axially thereto to extend the actuator means toward the clip in the cradle, successively closing the open jaw of the clip and moving the clasp to locking position;

and spring biased stop means for limiting retraction of the actuator means to a first rearward limit position when a reverse thumb force is applied to the actuator means and resistively permissive of further retraction of the actuator means by an additional reverse thumb force applied to the actuator means.

12. An applicator according to claim 11 having spring detent means offering resistance to forward movement of the actuator means for moving the clasp to locking position.

* * * * *